United States Patent [19]

Lawless et al.

[11] Patent Number: 5,078,362

[45] Date of Patent: Jan. 7, 1992

[54] SPRING-BIASED VALVE FOR USE IN A POSITIVE DISPLACEMENT VOLUMETRIC PUMP

[75] Inventors: Michael W. Lawless, Boulder Creek; Vernon R. Natwick, Los Altos, both of Calif.

[73] Assignee: Abbott Laboratories, Abbott Park, Ill.

[21] Appl. No.: 711,117

[22] Filed: Jun. 4, 1991

Related U.S. Application Data

[63] Continuation of Ser. No. 494,209, Mar. 15, 1990, abandoned.

[51] Int. Cl.⁵ .............................................. F16K 7/06
[52] U.S. Cl. .............................................. 251/9; 251/4
[58] Field of Search .................... 251/4, 7, 9; 137/844

[56] References Cited

U.S. PATENT DOCUMENTS

| | | | |
|---|---|---|---|
| 2,412,397 | 12/1946 | Harper | 103/148 |
| 3,384,336 | 5/1968 | Pulman | 251/9 |
| 3,609,069 | 9/1971 | Martinelli | 417/474 |
| 4,277,226 | 7/1981 | Archibald | 417/38 |
| 4,302,164 | 11/1981 | Manella | 417/474 |
| 4,391,600 | 7/1983 | Archibald | 604/153 |
| 4,424,832 | 1/1984 | Koda | 137/844 |
| 4,479,797 | 10/1984 | Kobayashi et al. | 604/153 |
| 4,559,038 | 12/1985 | Berg et al. | 604/153 |
| 4,634,092 | 1/1987 | Daniell et al. | 251/7 |
| 4,650,469 | 3/1987 | Berg et al. | 604/131 |
| 4,653,987 | 3/1987 | Tsuji et al. | 417/360 |
| 4,690,673 | 9/1987 | Bloomquist | 604/67 |
| 4,728,265 | 3/1988 | Cannon | 417/363 |

Primary Examiner—John C. Fox
Attorney, Agent, or Firm—Christensen, O'Connor, Johnson & Kindness

[57] ABSTRACT

A "cracking valve" for use in a volumetric pump. A volumetric pump (30) includes a plunger (48) for compressing a pumping portion (34b) of a flexible tubing that extends through the pump. An inlet cracking valve (46) and an outlet cracking valve (52) are disposed so that they compress the flexible tubing to control fluid flow therethrough. The inlet cracking valve operates in three modes, including a fully open mode, a closed mode that stops fluid flow through the flexible tubing, and a cracking mode. The outlet cracking valve only operates in the closed mode and the cracking mode. As the plunger compresses the flexible tubing, fluid pressure within the pumping portion of the flexible tubing initially builds until it exceeds a predefined cracking pressure, forcing open the inlet cracking valve, which is in its cracking mode, so that excess fluid is forced back to a container (32). After the pumping portion of the flexible tubing is compressed to a predefined volume, fluid at the cracking pressure is forced through the outlet cracking valve, which is then in its cracking mode. To compensate for changes in the elasticity or stiffness of the flexible tubing, balance blocks (42, 58) cooperate with the inlet cracking valve and the outlet cracking valve, respectively. The balance force developed by the balance block as a function of the stiffness of the flexible tubing is added to the force of a cracking flexure to produce the desired predefined cracking force at the inlet cracking valve and the outlet cracking valve. A "T-shaped" formation comprising a transverse ridge (166) and a longitudinal ridge (168) comprises valve faces (106a, 106b) at both cracking valves. The transverse ridge controls fluid flow, whereas the longitudinal ridge has a surface area over which the fluid pressure within the pumping portion of the flexible tubing acts to overcome the cracking force.

30 Claims, 9 Drawing Sheets

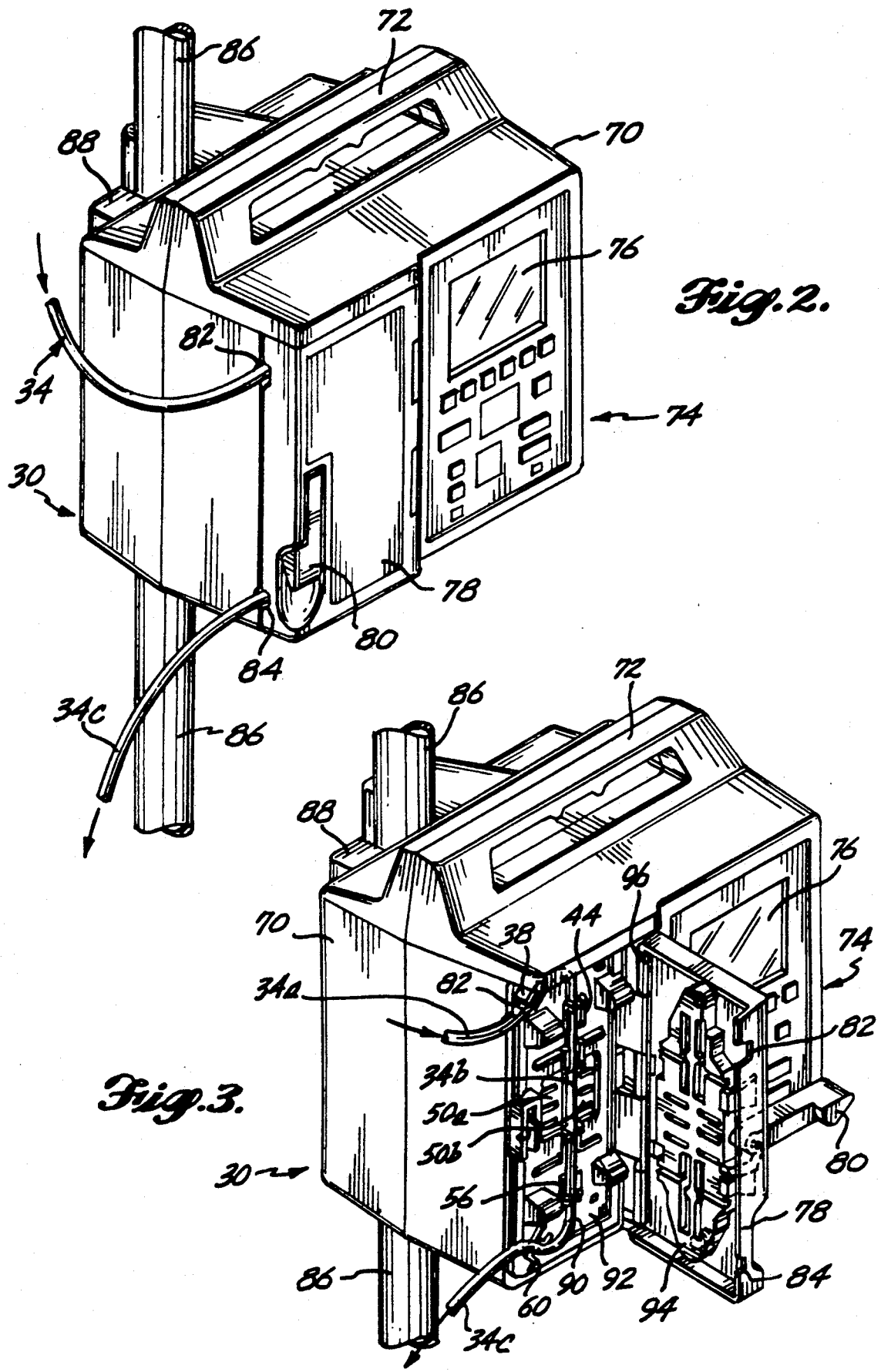

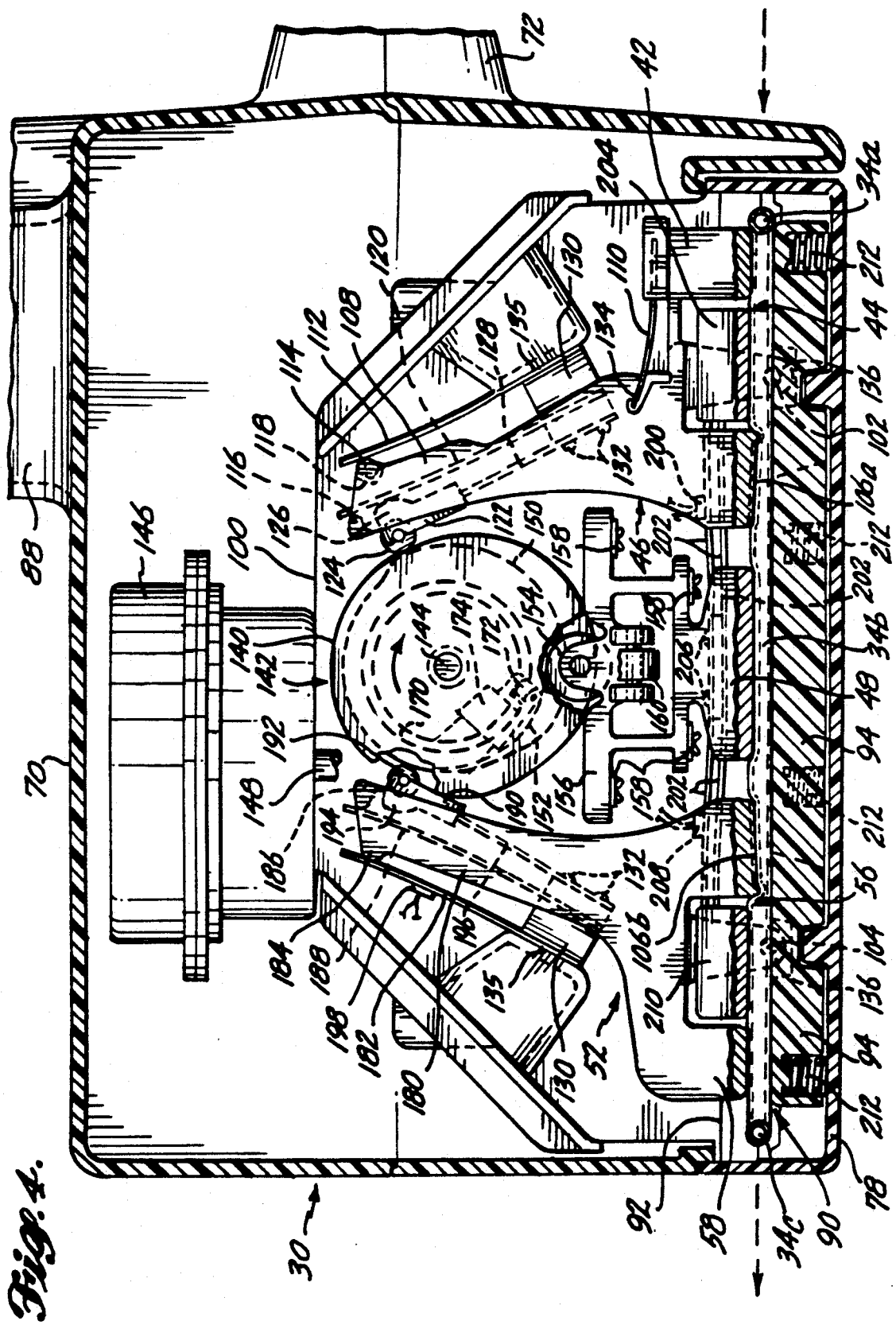

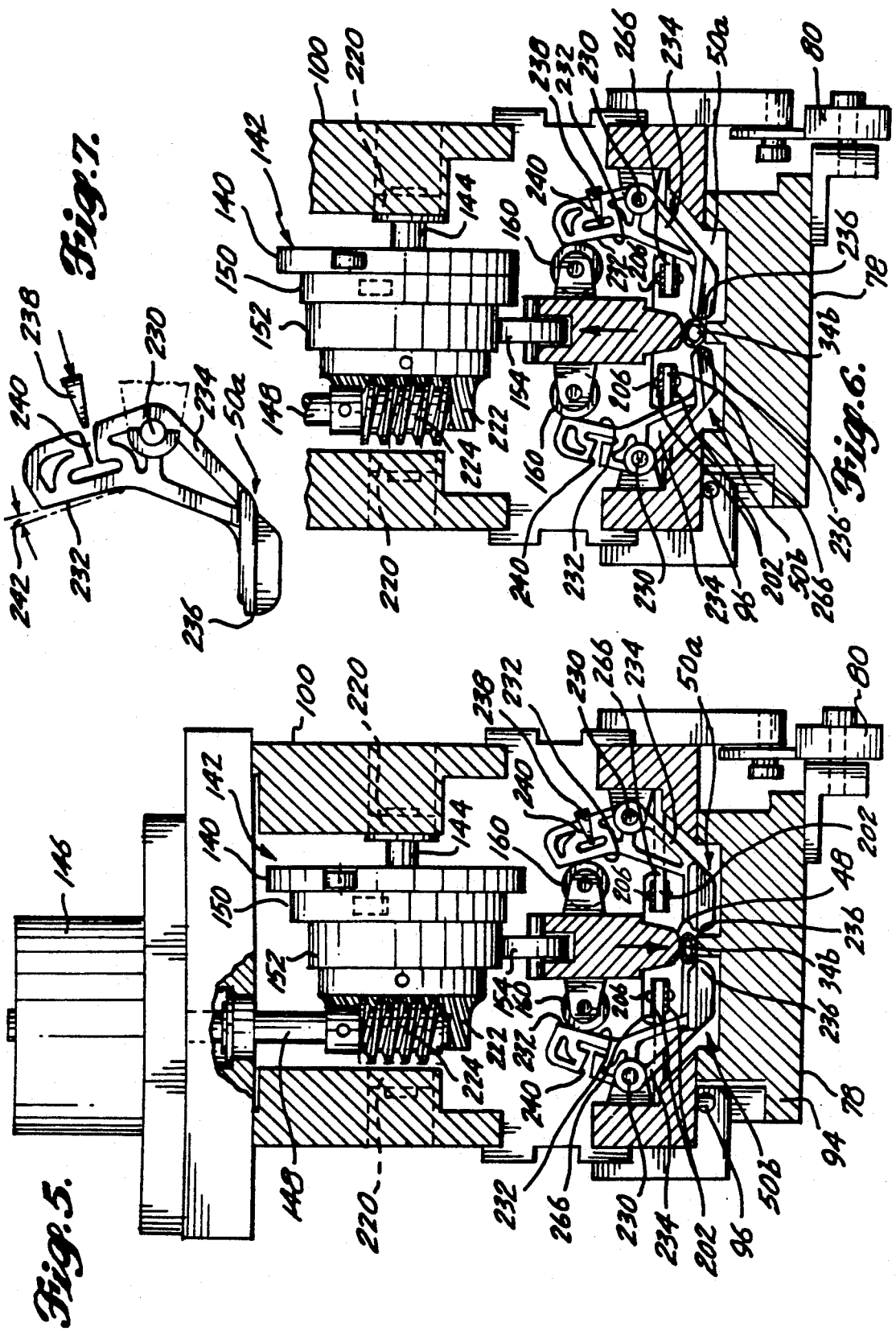

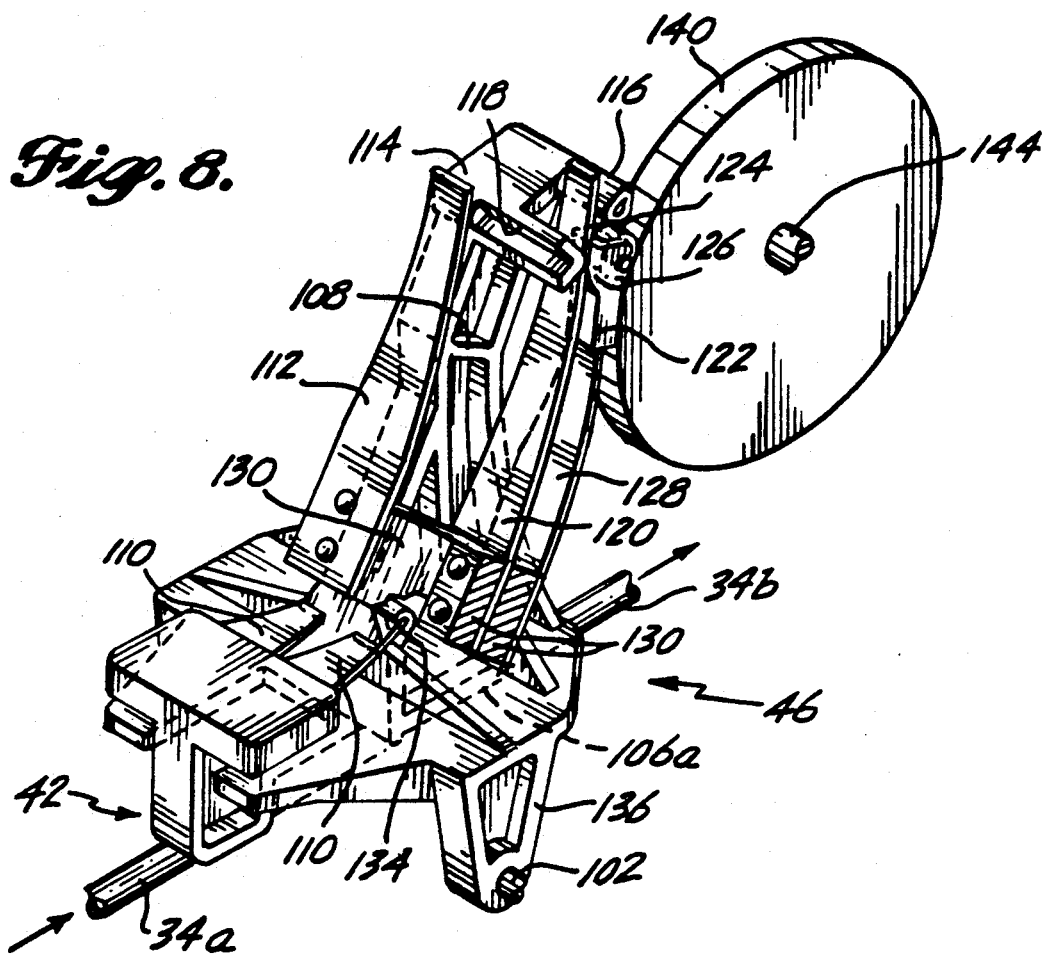
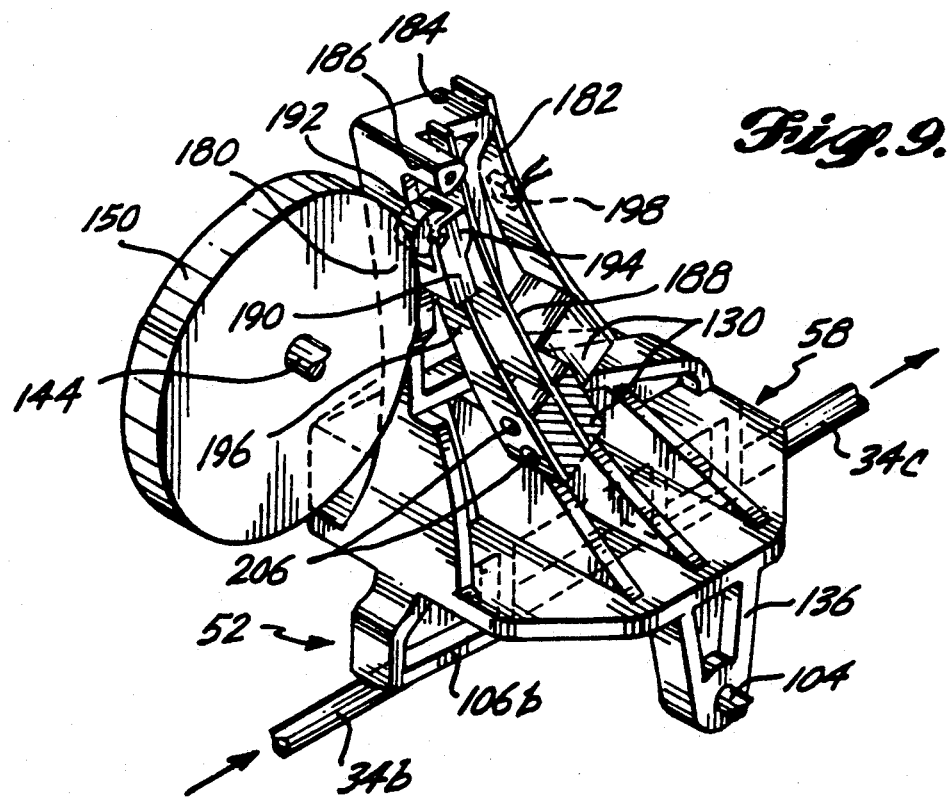

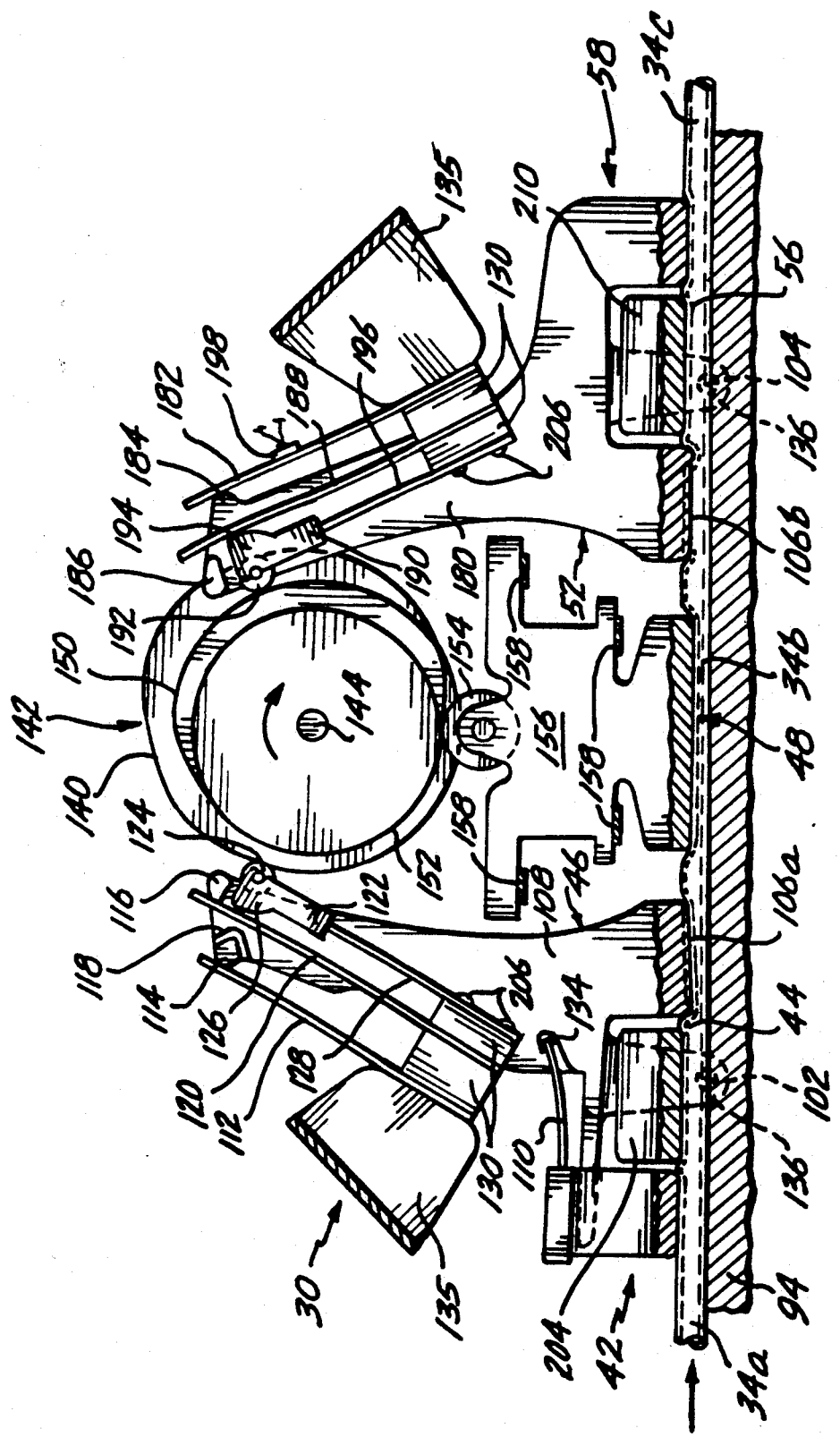

SPRING-BIASED VALVE FOR USE IN A POSITIVE DISPLACEMENT VOLUMETRIC PUMP

This application is a continuation application based on prior copending application Ser. No. 07/494,209, filed on Mar. 15, 1990 now abandoned.

TECHNICAL FIELD

This invention generally pertains to pump valves, and specifically, to a valve for use in a volumetric pump that displaces fluid within a tube by compressing the tube.

BACKGROUND OF THE INVENTION

Intravenous administration of medicinal liquids has traditionally been accomplished using a drip-regulated gravity flow system. A more precisely regulated flow of the infused liquid generally can be achieved using a pump to advance the liquid at a predefined rate. For this reason, a peristaltic pump is often used to administer drugs intravenously through a continuous line that extends directly from a bag or bottle reservoir to the patient. The IV line of flexible tubing is threaded into a channel formed within the peristaltic pump body, and this section of the flexible tubing is compressed to displace fluid from the pump.

In one type of peristaltic pump, rollers are mounted on each end of a rotating arm. These rollers advance along the longitudinal axis of the flexible tubing as the arm rotates, thereby compressing the tubing and displacing a bolus of fluid from the pump ahead of each advancing roller.

Another type of positive displacement peristaltic pump includes a plurality of fingerlike plungers that are sequentially actuated to compress a section of flexible tubing, thus defining an advancing point of compression that forces fluid through the tubing and out of the pump. The plungers are typically actuated by a plurality of cams disposed along a motor driven shaft. An example of such a pump is described in U.S. Pat. No. 4,479,797.

The flow rate of a fluid being administered with a peristaltic pump is normally controlled by varying the speed of the rotating arm or the rotational speed of the cams that transfer the force to displace fluid in the flexible tubing. Changes in the volume of the flexible tubing that extends through the pump can significantly affect the rate that fluid is dispensed by the pump. The disposable tube sets employed to intravenously administer drugs typically comprise polyvinyl chloride (PVC). Continued flexure of PVC tubing eventually degrades its ability to elastically recover from the compressed state to its full uncompressed state as the compression force is removed. Even during its initial use in the pump, PVC tubing returns to its uncompressed shape relatively slowly. Thus, a change in the tube's elasticity over time can vary the volume of liquid advanced by a peristaltic pump during each pumping cycle or stroke. This variation in tubing elasticity or stiffness appears as an error in the rate at which fluid is delivered by the pump.

Tube shapers have been used in peristaltic pumps to force the flexible tubing to open up to its uncompressed shape and to compensate for the inadequate elasticity of the low cost PVC tubing sets usually used in peristaltic pumps. The tube shaper laterally squeezes the compressed tubing as the pumping compression force is withdrawn or reduced, to force the tubing to resume its round, uncompressed configuration. By restoring the tubing to its fully uncompressed state after each periodic pumping compression, the volume of the internal passage filling with fluid remains generally constant, even after extended use of the tubing in the pump. As an alternative to use of a tube reshaper, silicon tubing, which has much better elastic properties than PVC tubing, can be used within a peristaltic pump, but this approach adds substantially to the cost of the disposable tubing set.

In a copending, commonly assigned U.S. patent application entitled, "Volumetric Pump With Spring-Biased Cracking Valves," Ser. No. 07/742,623, filed 8 Aug. 1991, a novel type of positive displacement volumetric pump is disclosed that provides a much more accurate and constant rate of flow than can be achieved using a conventional peristaltic pump. The volumetric pump disclosed in this patent application displaces fluid from within a section of flexible tubing disposed between spring-biased inlet and outlet valves. The inlet valve is forced open by fluid at a predefined "cracking pressure," as the section of tubing is initially compressed, thereby permitting excess fluid within the compressed section to backflow toward a source container. The inlet valve then closes fully, and the outlet valve "cracks open" in response to the cracking pressure, enabling a predefined volume of fluid at the predefined cracking pressure, to flow from the pump to the patient.

Clearly, variations in tubing stiffness or elasticity could affect the cracking pressure and thus the accuracy of the rate at which this volumetric pump delivers fluid. Therefore, the effect of variations in the elasticity of the flexible tubing used in this novel volumetric pump is somewhat analogous to the effect of changes in the elasticity of such tubing when used in a conventional peristaltic pump.

Accordingly, to maintain an accurate rate of fluid flow from the novel volumetric pump briefly described above, it is an object of the present invention to compensate for variations or changes in the stiffness or elasticity of flexible tubing from which fluid is displaced when the tubing is compressed. It is a further object to provide a pump valve for use in the volumetric pump that is biased closed by a spring, but opens when fluid pressure in the tube reaches a predefined level, substantially independent of variations in tube stiffness or elasticity. Yet a further object is to vary the force acting to bias the pump valve closed to compensate for variations in the stiffness or elasticity of the flexible tube, so that a substantially constant pressure is required to force the valve open. Yet a further object is to provide a pump valve having a surface that applies a compression force to the tubing to control fluid flow therethrough, a fluid pressure within the tube acting on this surface to provide a force in opposition to the compression force, to force fluid through the tubing at a predefined pressure. These and other objects and advantages of the present invention will be apparent from the attached drawings and the Description of the Preferred Embodiment that follows.

SUMMARY OF THE INVENTION

In accordance with the claims, a valve for controlling fluid flow through a passage defined by an elastomeric member includes a frame having backing means for supporting the elastomeric member. Pivotally mounted to the frame for rotation about a pivot axis and positioned on an opposite side of the passage from the backing means is a valve member. The valve member includes disparate first and second surfaces that contact the elastomeric member with opposing forces on opposite sides of the pivot axis. A spring is mounted between the frame and the valve member and contributes to a cracking force applied to the valve member, tending to pivot the valve member about the pivot axis to compress the elastomeric member between the first surface and the backing means. The valve member thus closes the passage between the first surface and backing member until the pressure of a fluid within the passage exceeds a predetermined cracking pressure, at which point, the cracking pressure forces open the passage. As the passage is forced open, fluid begins to flow through the passage. The force developed by the contact of the second surface of the valve member with the elastomeric member also contributes to the cracking force by an amount that depends on an elasticity of the elastomeric member, thereby compensating for any changes in the elasticity of the elastomeric member that would otherwise vary the cracking pressure. The elastomeric member preferably comprises a flexible tubing.

The valve further includes closure means for pivoting the valve member so that the first surface compresses the elastomeric member with a relatively greater force than the cracking force, thereby closing the passage and preventing fluid flow through the passage, independently of the cracking pressure. The closure means comprises a second spring mounted between the housing and the valve member. To block fluid flow through the passage, the second spring is selectively controlled to increase the compression force applied by the valve member against the elastomeric member. Also included on the valve member, in one embodiment, is a spring link connecting a first portion of the valve member on which the first surface is disposed to a second portion of the valve member on which the second surface is disposed. In this embodiment, the spring link preferably comprises a thin metal flexure having sufficient elasticity to enable the first portion of the valve member to assume a position in which the passage between the first portion of the valve member and the backing means is open. To open the passage, the first portion of the valve member pivots further away from the elastomeric member than the second portion; the elastomeric member is then substantially uncompressed, both between the first surface and the backing means and between the second surface and the backing means. Means for pivoting the first surface away from the elastomeric member, in opposition to the cracking force, are provided to open the passage.

A method for compensating a cracking valve for changes in the elasticity of a flexible member that defines a passage through which fluid is pumped comprises another aspect of this invention. The method includes steps generally consistent with the functions of the elements comprising the cracking valve, as set forth above.

The invention also relates to another aspect of a cracking valve for controlling the flow of a pressurized fluid through flexible tubing. The cracking valve includes a pivotally mounted valve member that has an elongate surface for applying a compressive force to the flexible tubing. The surface in contact with the flexible tubing comprises a generally "T"-shaped formation, which is defined by a transverse ridge and a longitudinal ridge, the latter being aligned with a longitudinal axis of the flexible tubing, and the transverse ridge running transverse to the longitudinal axis. A spring biases the valve member to pivot the surface into contact with the flexible tubing with a flow control force sufficient for the transverse ridge to block fluid flow through the flexible tubing until the pressure of the fluid in the tubing exceeds a predetermined cracking pressure. The pressure of the fluid acts through the flexible tubing over an area of the surface encompassing the longitudinal ridge to achieve a force that exceeds the flow control force. As a result, a passage is opened in the flexible tubing through which fluid flows past the transverse ridge.

In the cracking valve, the transverse and longitudinal ridges are preferably defined, at least in part, by curves having radii that do not exceed a conforming curve readily achievable by the flexible tubing. The transverse ridge is disposed on the surface so as to contact the flexible tubing at a point farther from the pressurized fluid than where the longitudinal ridge contacts the flexible tubing. Preferably, the longitudinal ridge is at least twice as long as the diameter of the flexible tubing and extends outwardly of the surface of the valve member with an elevation that is greater proximal the transverse ridge than distal thereto.

Further comprising the cracking valve are means for compensating for variations in the elasticity of the flexible tubing to minimize changes in the cracking pressure. The means for compensating comprise a second surface in contact with the flexible tubing; this second surface and the first surface are disposed on opposite sides of a pivot axis about which the valve member pivots.

BRIEF DESCRIPTION OF THE DRAWINGS

FIG. 2 is an isometric view of the volumetric pump, showing an access door closed and latched in place;

FIG. 3 is an isometric view, similar to that shown in FIG. 2, but with the access door shown in an open position, disclosing the path followed by flexible tubing through the volumetric pump;

FIG. 4 is a longitudinal cross section of the pump assembly shown in FIGS. 2 and 3;

FIG. 5 is a schematic transverse cross section of the volumetric pump, illustrating compression of the flexible tubing to pump fluid;

FIG. 6 is a schematic cross section of the volumetric pump, illustrating reshaping of the flexible tubing to facilitate its filling with fluid;

FIG. 7 is a plan view illustrating the calibration of one of the tubing reshaping arms to achieve a desired angular deflection;

FIG. 8 is an isometric view of an inlet cracking valve in accordance with the present invention and a transverse section of a cam assembly that is used to actuate the inlet cracking valve;

FIG. 9 is an analogous view to that of FIG. 8, isometrically showing an outlet cracking valve in accordance with the present invention and a transverse section of the cam assembly that is used to actuate the outlet cracking valve;

FIGS. 10A-10C are cutaway longitudinal cross sections of the volumetric pump, illustrating the disposition of components of the volumetric pump during a fill segment, a pumpback-pressurization segment, and a pumping segment of the pumping cycle;

DESCRIPTION OF THE PREFERRED EMBODIMENTS

The term "volumetric pump" is used in connection with an application for the present invention because it appropriately emphasizes one of the more important advantages that derives from the use of the invention. Specifically, during each pumping stroke, the volumetric pump consistently and repeatedly displaces a defined volume of fluid at a defined pressure, thereby ensuring that a desired rate of fluid flow is accurately provided by the pump.

Figure 1:
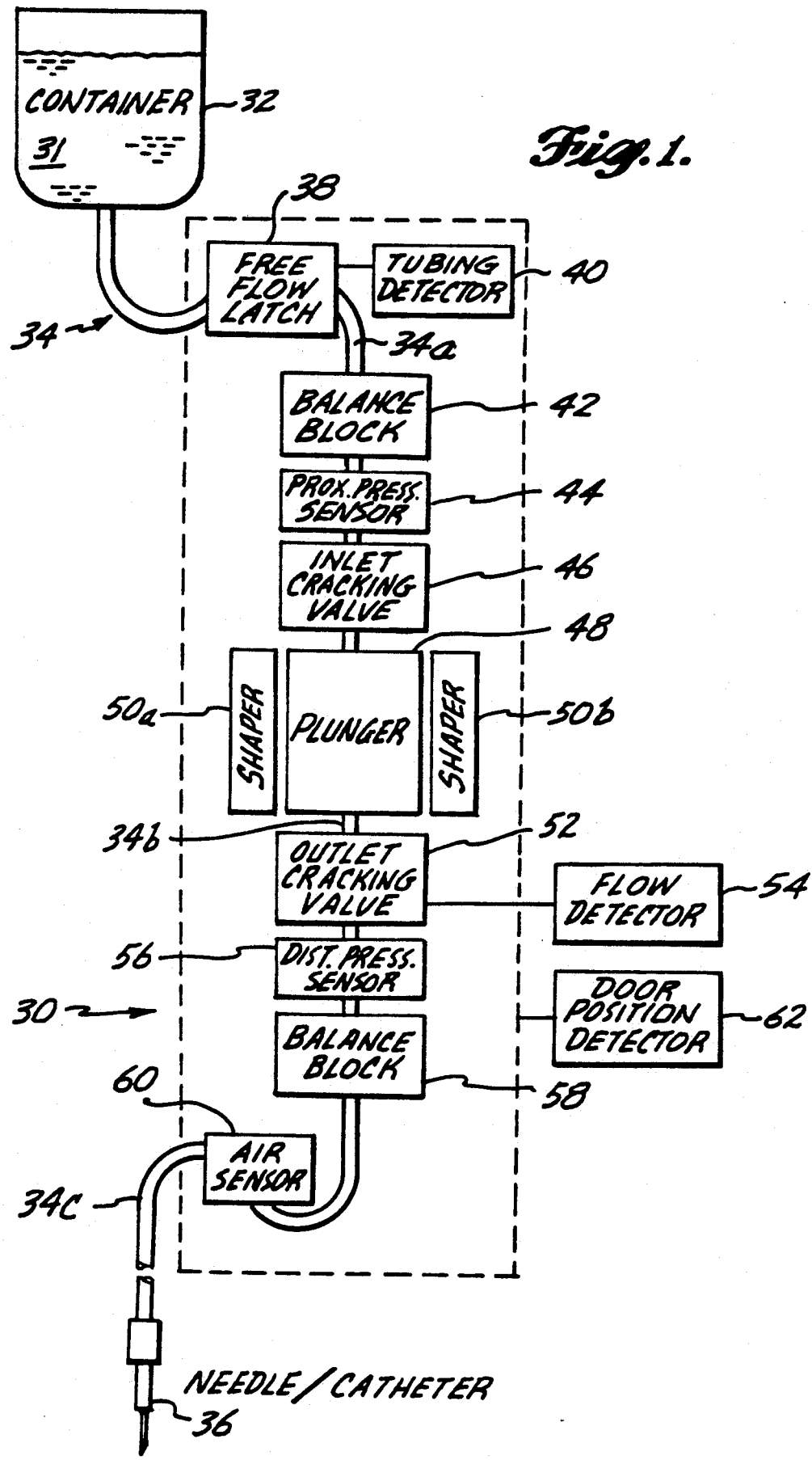
FIG. 1 is a schematic block diagram of a volumetric pump in which the present invention is used.

In FIG. 1, a volumetric pump is generally illustrated in block diagram at reference numeral 30. Volumetric pump 30 comprises a number of components that are serially arranged along a fluid path through the pump. A liquid 31 that is administered by volumetric pump 30 is supplied from a container 32 through flexible tubing 34. Liquid 31 enters volumetric pump 30 through a proximal portion 34a of the flexible tubing. The fluid path continues through a pumping portion 34b and exits the pump through a distal portion 34c of the flexible tubing. Distal portion 34c of the flexible tubing is connected to a needle/catheter 36 that is used to introduce liquid 31 output from the pump intravenously into a patient. Of course, volumetric pump 30 may also be used in other applications wherein distal portion 34c of the flexible tubing is connected to some other apparatus disposed downstream of volumetric pump 30.

Flexible tubing 34 is continuous, but for purposes of this disclosure, is referred to as divided into the proximal, pumping, and distal portions 34a, 34b, and 34c, respectively; preferably, it comprises a polyvinyl chloride (PVC) disposable tube set, such as is customarily used to administer fluids intravenously to a patient. The tubing may have a 0.137" O.D. and 0.100" I.D.

In this application of the volumetric pump, it is desirable to prevent free flow of liquid 31 from container 32 into the patient. For this reason, volumetric pump 30 includes a free flow latch 38, which clamps proximal portion 34a of the flexible tubing to prevent liquid 31 from container 32 flowing freely into a patient, due to head pressure. Free flow latch 38 does not restrict fluid flow during the normal pumping operation of volumetric pump 30, but is configured to automatically clamp proximal portion 34a of the flexible tubing when a door 78 (shown in FIGS. 2 and 3) on volumetric pump 30 is opened. While door 78 is closed, free fluid flow through volumetric pump 30 is otherwise precluded by volumetric pump 30, as explained below. The position of door 78 is sensed by a door position detector 62, producing a signal that prevents operation of volumetric pump 30 when door 78 is open. Similarly, a tubing detector 40 is interconnected to free flow latch 38, and produces a signal indicative of the presence of flexible tubing 34 within free flow latch 38; operation of volumetric pump 30 is inhibited if the signal indicates that the flexible tubing is not in place.

A balance block 42 rests against proximal portion 34a of the flexible tubing and serves to compensate for variations or changes in the elasticity of flexible tubing 34. The function and operation of balance block 42 is more fully explained below.

Next in the serial arrangement of components along the fluid path within volumetric pump 30 is a proximal pressure sensor 44, which operates to sense the pressure of fluid within proximal portion 34a of the flexible tubing. Proximal pressure sensor 44 produces a signal indicative of fluid pressure in this portion of the flexible tubing 34 for use in monitoring the operation of the pump and to determine if proximal portion 34a has become occluded.

A key element in the operation of volumetric pump 30 is an inlet cracking valve 46, disposed immediately downstream of proximal pressure sensor 44. Inlet cracking valve 46 functions in cooperation with a plunger 48 and an outlet cracking valve 52, which are disposed sequentially downstream of the inlet cracking valve, to provide the displacement of a volumetric quantity of fluid from pumping portion 34b of the flexible tubing by volumetric pump 30 and to generally isolate the volumetric pump from variations in proximal and distal fluid pressure, due for example, to variations in the elevation of container 32, or variations in the back pressure of fluid in distal portion 34c of the flexible tubing. A flow detector 54 is interconnected with outlet cracking valve 52 and produces a signal indicating whether fluid is successfully being pumped by volumetric pump 30 into distal portion 34c. Tubing shapers 50a and 50b are disposed at each side of plunger 48 and act to rapidly reform pumping portion 34b of the flexible tubing as it refills with fluid during each pump cycle, insuring consistent volumetric refill with each pumping stroke.

A distal pressure sensor 56 produces a signal indicative of the fluid pressure within distal portion 34c of the flexible tubing, i.e., the output pressure of volumetric pump 30. The distal fluid pressure is used for monitoring the operation of volumetric pump 30 and for sensing an occlusion of flexible tubing 34.

Immediately adjacent distal pressure sensor 56 is a balance block 58. Cooperating with outlet cracking valve 52, balance block 58 compensates for changes or variations in the stiffness or elasticity of flexible tubing 34, in a manner similar to that in which balance block 42 cooperates with inlet cracking valve 46.

An air sensor 60 is the last component along the fluid path through volumetric pump 30. Air sensor 60 detects the presence of air bubbles larger than a predefined volume in the fluid discharged from the volumetric pump, and produces a signal indicative of such air bubbles, which stops volumetric pump 30 and initiates an alarm to prevent a potentially harmful air embolism forming in the fluid being introduced into a patient through needle/catheter 36. Air sensor 60 generally comprises a conventional piezoelectric ultrasonic transmitter and receiver (not separately shown), which are disposed on opposite sides of distal portion 34c of the flexible tubing. The transmitter produces an ultrasonic signal that is transmitted through flexible tubing 34 to the receiver. Liquid present in flexible tubing 34 between the transmitter and receiver conveys the ultrasonic signal much more efficiently than does an air bubble. The receiver produces an electronic signal in response to the level of the ultrasonic signal reaching it, the amplitude of the electronic signal indicating whether an air bubble or liquid is present in flexible tubing 34 between the transmitter and receiver. Details of air sensor 60 are not illustrated because such devices are generally well known to those of ordinary skill in this art.

In FIGS. 2 and 3, volumetric pump 30 is illustrated in isometric view. As shown therein, volumetric pump 30 includes a molded plastic housing 70, having a handle 72 on its upper surface to facilitate carrying the volumetric pump to a point of use. A control panel 74 and a display 76 are disposed on the right side of the front surface of volumetric pump 30, and are respectively used by an operator for entry and display of data that controls the volumetric pump.

On the back of housing 70 is formed a clamp 88, which is used to removably attach volumetric pump 30 to a post 86, for example at the bedside of a patient. Details of clamp 88 are not shown, since it is generally typical of those used with other types of medical apparatus intended for connection to vertical posts.

In FIG. 2, door 78 is shown latched closed, the appropriate disposition for use of the volumetric pump, while in FIG. 3, door 78 is shown in an open position. A latch handle 80 is pivoted upwardly, so that door 78 can be swung open on a hinge 96, giving access to an inner cover 92 that defines the path followed by flexible tube 34 through volumetric pump 30. As noted above, when door 78 is opened while flexible tubing 34 is threaded through the volumetric pump and connected to container 32, free flow latch 38 clamps the flexible tubing closed to prevent liquid 31 in container 32 from free flowing through flexible tubing 34. The mechanism that actuates free flow latch 38 when door 78 is opened is not shown, since it is not particularly relevant to the present invention.

Flexible tubing 34 is angled upwardly where it passes through an entry slot 82 formed on the side of door 78, insuring that any of liquid 31 leaking from container 32 drips from a loop formed in flexible tubing 34 and does not run into volumetric pump 30. After door 78 is swung open, flexible tubing 34 is readily threaded into a channel 90 defined along the longitudinal center of inner cover 92. An exit slot 84 formed in the lower side portion of door 78 overlies distal portion 34c of the flexible tubing. A pressure plate 94 disposed on the inner surface of door 78 comes into contact with flexible tubing 34 along the length of channel 90 as door 78 is closed and latched with handle 80.

FIGS. 4, 5 and 6 show details of the interior of volumetric pump 30. Pressure plate 94 defines a reference plane or surface in respect to each of the components of volumetric pump 30 that act to compress flexible tubing 34 and is mounted so that it floats on a plurality of helical coiled springs 212, which bias the pressure plate away from the inner surface of door 78. When door 78 is closed, pressure plate 94 contacts inner cover 92 at several points. Helical springs 212, which are relatively stiff, are thus slightly compressed, and therefore accommodate variations in the tolerances of door 78 and other related parts that arise during construction of volumetric pump 30. Such tolerances might otherwise affect the position of the reference plane defined by pressure plate 94.

Most of the components comprising volumetric pump 30 are mounted on a frame 100 within housing 70. For example, frame 100 includes inlet cracking valve pivot mounts 102 and outlet cracking valve pivot mounts 104, about which inlet cracking valve 46 and outlet cracking valve 52 respectively pivot.

Inlet cracking valve 46 contacts proximal portion 34a of the flexible tubing along a valve face 106a. Similarly, outlet cracking valve 52 contacts distal portion 34c of the flexible tubing along a valve face 106b. The pivotal motion of inlet cracking valve 46 and outlet cracking valve 52 respectively varies the force with which valve faces 106a and 106b contact flexible tubing 34 to control fluid flow therethrough by compressing the flexible tubing against pressure plate 94. Plunger 48 compresses pumping portion 34b of the flexible tubing against pressure plate 94 to displace fluid from within a pumping chamber defined between the inlet and outlet cracking valves 46 and 52. In part because volumetric pump 30 includes inlet and outlet cracking valves 46 and 52, it operates differently than the prior art plunger type peristaltic pumps, as will be apparent from the following disclosure.

An inlet valve arm 108 extends upwardly from valve face 106a on inlet cracking valve 46. Disposed generally above inlet cracking valve pivot mounts 102 are flat spring steel flexures 110, which connect balance block 42 to a slot 134, formed on the back side of valve arm 108. Flexures 110 are snapped within slot 134 and flex to enable inlet valve arm 108 to pivot valve face 106a away from pressure plate 94 through a greater angle than would otherwise be possible, without closing off fluid flow through flexible tubing 34 due to compression of the flexible tubing by balance block 41. Inlet cracking valve pivot mounts 102 are connected to downwardly depending pivot arms 136 on inlet cracking valve 46, at each side of flexible tubing 34, and centered between balance block 42 and valve face 106a. The stiffness of flexible tubing 34 acts on balance block 42 and flexures 110, and the balance force developed as a function of this stiffness (or lack of elasticity) tends to pivot inlet valve face 106a against pressure plate 94, increasing the force exerted by that part of inlet cracking valve 46 to compress the flexible tubing. Of course, the stiffness of flexible tubing 34 also resists compression by inlet valve face 106a to a similar extent. Accordingly, variations in the elasticity of flexible tubing 34 that affect the force required for inlet valve face 106a to compress the tubing are automatically compensated by balance block 42.

Inlet cracking valve 46 operates in three distinct modes, in each of which, the force applied by valve face 106a to compress flexible tubing 34 is substantially different. Two different spring-bias forces act on inlet valve arm 108. A fluid flow control force is applied to inlet valve arm 108 by a flat metal spring cracking flexure 112, acting against a knob 114, which is disposed at one end of inlet valve arm 108. The additional force necessary to compress flexible tubing 34 sufficiently to completely close off fluid flow past inlet cracking valve 46 is supplied by a flat metal spring closure flexure 120. Closure flexure 120 acts upon a side arm 116, disposed on one side of inlet valve arm 108. The combined force provided by cracking flexure 112 and closure flexure 120 (in addition to the balance force provided by balance block 42) pivots inlet cracking valve 46 about a pivot axis extending through inlet cracking valve pivot mounts 102, to completely block fluid flow through flexible tubing 34.

An inlet valve cam follower 122 selectively determines whether cracking flexure 112 and closure flexure 120 apply force against inlet valve arm 108 and thus determine the three modes in which inlet cracking valve 42 operates. Inlet cam follower 122 includes a roller 124 rotatably mounted in a hood 126, which is attached via an inlet follower flexure 128 to a plurality of blocks 130. Blocks 130 are also used in mounting cracking flexure 112 and closure flexure 120 to a bracket 135 and provide appropriate spacing between these flexures and bracket 135. Bolts 132 connect the ends of each of these flexures to bracket 135, which comprises a portion of frame 100.

Roller 124 rolls along an inlet valve cam track 140, disposed on a rotating cam assembly 142. Cam assembly 142 turns on a camshaft 144, which at each of its ends, is mounted to frame 100 in bearings 220 (see FIGS. 5 and 6). A shaft 148 extends downwardly from a motor 146, and a helical gear 224 on motor shaft 148 drivingly engages gear teeth 222, which are formed on one end of cam assembly 142, causing the cam assembly to rotate in a clockwise direction, as viewed in FIG. 4. The radial distance between camshaft 144 and the point where roller 124 contacts the surface of inlet valve cam track 140 varies as cam assembly 142 rotates, moving inlet valve cam follower 122 radially back and forth so as to control the forces applied to inlet valve arm 108. Specifically, as hood 126 is forced radially back against closure flexure 120, it lifts the closure flexure away from side arm 116, eliminating the force normally exerted by the closure flexure against the side arm, and thereby reducing the total force exerted by valve face 106a against flexible tubing 34. In this configuration, inlet cracking valve 46 is in a "cracking mode."

As hood 126 moves further radially outward, closure flexure 120 contacts a "V-shaped" side arm 118, formed on the side of inlet valve arm 108, causing inlet valve arm 108 to pivot valve face 106a away from pressure plate 94. In this configuration, inlet cracking valve 46 is in an open mode, wherein liquid 31 freely flows from container 32 through proximal portion 34a of the flexible tubing and into pumping portion 34b. Flexures 110 bend as valve face 106a pivots away from pressure plate 94, so that balance block 42 does not close off fluid flow through proximal portion 34a of the flexible tubing.

When both closure flexure 120 and cracking flexure 112 are allowed to act on inlet valve arm 108, valve face 106a compresses flexible tubing 34 against pressure plate 94 sufficiently to completely block fluid flow through the flexible tubing. In this configuration, inlet cracking valve 46 is in a "closed mode."

An outlet valve cam track 150 is disposed between inlet valve cam track 140 and a plunger cam track 152. Plunger cam track 152 provides a surface at varying radii about camshaft 144 for actuating plunger 48 to compress pumping portion 34b of the flexible tubing against pressure plate 94. A roller 154 is rotatably mounted on a base 156 of plunger 48, and is thus disposed to roll along plunger cam track 152. Also mounted on base 156, at opposite sides of roller 154, are tube shaper rollers 160. The disposition of tube shaper rollers 160 is more clearly shown in FIGS. 5 and 6, and their operation in respect to shaping flexible tubing 34 is disclosed in detail below.

As shown using hidden lines in FIG. 4, the back side of cam assembly 142 includes a torque compensation track 170. A conically shaped torque compensation roller 172 rolls along torque compensation track 170, applying a rotational torque to cam assembly 142 that compensates for an opposite torque resulting from rapid changes in the shape of inlet valve cam track 140, outlet valve cam track 150 and plunger cam track 152. Torque compensation roller 172 is mounted on a flat metal spring torque compensation flexure 174 that applies a biasing force to cam assembly 142.

Like inlet cracking valve 46, outlet cracking valve 52 has a generally "Y-shaped" configuration, and includes an outlet valve arm 180, which is connected to outlet valve face 106b and to balance block 58. On opposite sides of flexible tube 34, pivot arms 136 extend downwardly, connecting to pivot mounts 104 on frame 100. Balance block 58 rests on distal portion 34c of the flexible tubing and develops a force proportional to the stiffness (or lack of elasticity) of flexible tubing 34, which tends to increase the compression force applied against flexible tubing 34 by outlet valve face 106b to compensate or balance the resistance to compression caused by the stiffness (or lack of elasticity) of the flexible tubing. (Hereafter, and in the claims, "elasticity" is used synonymously with "stiffness.") Just as balance block 42 compensates for changes or variations in elasticity of the flexible tubing in respect to inlet cracking valve 46, balance block 58 compensates for such changes and variations in respect to outlet cracking valve 52. However, since outlet cracking valve 52 is never pivoted to an open mode like inlet cracking valve 46, balance block 58 is integrally attached to outlet valve arm 180. Flexures 110 are not required, since the extent of pivotal rotation of outlet cracking valve 52 is substantially more limited than for inlet cracking valve 46. At all times, even when volumetric pump 30 is not pumping fluid, either inlet cracking valve 46 or outlet cracking valve 52 is in its closed mode, preventing liquid 31 from free flowing through flexible tubing 34.

As shown in FIG. 4, outlet cracking valve 52 is in its closed mode, compressing flexible tubing 34 against pressure plate 94 sufficiently to block fluid flow therethrough. In this configuration, a flat metal spring cracking flexure 182 applies force against a knob 184 on the top of outlet valve arm 180. In addition, a flat metal spring closure flexure 188 applies a biasing force against a side arm 186 that extends outwardly from the side of outlet valve arm 180.

An outlet valve cam follower 190 includes a roller 192, which rolls along outlet valve cam track 150. Roller 192 is rotatably mounted within a hood 194, which is connected to a flat metal spring follower flexure 196. Follower flexure 196 spring biases roller 192 into contact with outlet cam track 150. The lower end of follower flexure 196 and the lower ends of cracking flexure 182 and closure flexure 188 are secured at blocks 130 to bracket 135 by bolts 132, just as the corresponding elements are in respect to inlet cracking valve 46. As outlet valve cam follower 190 follows outlet cam track 150, hood 194 periodically contacts closure flexure 188, lifting it away from side arm 186, so that the flow control force provided by cracking flexure 182, added to the balance force developed by balance block 58 is transmitted to valve face 106b, thereby compressing flexible tubing 34 against pressure plate 94 with a cracking force. In this configuration, outlet valve 52 is in its cracking mode.

As plunger 48 compresses pumping portion 34b of the flexible tubing against pressure plate 94, the pressure developed by liquid trapped between inlet cracking valve 46, which is closed, and outlet cracking valve 52 acts on valve face 106b, in opposition to the cracking force produced by cracking flexure 182 and balance block 58. As the force developed by the fluid pressure reaches a predetermined level sufficient to cause outlet cracking valve 52 to pivot open slightly, liquid 31 flows past the outlet cracking valve from pumping portion 34b of the flexible tubing. Liquid 31 is thus delivered by volumetric pump 30 at a predefined cracking pressure.

A strain gauge 198 is mounted to cracking flexure 182. Strain gauge 198 develops an output signal corresponding to the stress developed in cracking flexure 182, and therefore indicating the pivotal motion of outlet valve arm 180 as it rotates to allow fluid flow past outlet cracking valve 52. Accordingly, strain gauge 198 comprises a flow detector for determining whether fluid is being pumped through distal portion 34c of the flexible tubing as a result of displacement by plunger 48. If pumping portion 34b of the flexible tubing contains a relatively large proportion of air or other compressible gaseous fluid, plunger 48 cannot develop sufficient fluid pressure to overcome the cracking force exerted by cracking flexure 182 and balance block 58. As a result, strain gauge 198 fails to detect the pivotal motion of outlet valve arm 180, indicating that fluid flow past outlet cracking valve 52 has not occurred during a pumping stroke of plunger 48. Accordingly, the signal from strain gauge 198 can be used to detect whether container 32 has run dry, or whether flow of liquid 31 into volumetric pump 30 has otherwise been interrupted. The signal produced by strain gauge 198 is simply a "go/no-go" signal as opposed to a signal that is accurately proportional to the movement of outlet valve arm 180. This go/no-go signal is used to stop volumetric pump 30 and to initiate an alarm when the expected fluid flow is not obtained, thereby alerting medical personnel of the problem, so that it can be corrected.

Instead of strain gauge 198, various other types of motion sensors may be used to produce a signal indicative of the pivotal motion of outlet valve arm 180. For example, outlet valve arm 180 can be connected to a linear variable displacement transformer (LVDT) that uses motion to produce a signal corresponding to a relative change in the magnetic coupling between two electromagnetic coils, or may comprise a variable capacitor that changes capacitance value as outlet valve arm 180 pivots. Similarly, a Hall sensor or optical sensor can be used to detect pivotal motion of outlet valve arm 180, and thus may serve as alternative types of flow detectors.

Proximal pressure sensor 44 comprises a block 204, which is spring-biased into contact with proximal portion 34a of the flexible tubing, and is disposed between inlet cracking valve 46 and balance block 42. A spring-bias force for proximal pressure sensor 44 is provided by two pairs of longitudinally extending flexures 202, disposed on each side of plunger 48. Flexures 202 are connected to support plates 266 on frame 100 by fasteners 206 at about the midpoint of the flexures. One of the four flexures 202 connecting block 204 to support plates 266 includes a strain gauge 200, which responds to stress developed in that flexure 202 as a function of fluid pressure within proximal portion 34a of the flexible tubing. As the fluid pressure increases within this portion of flexible tubing 34, flexures 202 connected to block 204 experience increased stress, producing a corresponding change in the output signal from strain gauge 200.

Similarly, distal pressure sensor 56 comprises a block 210, which is connected to the other ends of flexures 202. A strain gauge 208 is disposed on one of the four flexures, intermediate block 210 and one of the support plates 266. Strain gauge 208 produces a signal corresponding to the fluid pressure within distal portion 34c of the flexible tubing, based upon stress developed in flexures 202 as a result of that pressure. Distal pressure sensor 56 can be used to determine if distal portion 34c of the flexible tubing has been kinked, interrupting fluid flow through flexible tubing 34, for example, as might occur if a patient rolled over onto flexible tubing 34. Such a condition causes a notable increase in the distal fluid pressure that triggers an alarm and shuts off volumetric pump 30.

In FIGS. 5, 6, and 7, details of tube shapers 50a and 50b are disclosed. Since it is preferable to use relatively low cost PVC tubing in connection with volumetric pump 30, tube shapers 50a and 50b are provided to ensure consistent operation and volumetric capacity of pumping portion 34b of the flexible tubing throughout the entire operating range of volumetric pump 30. At relatively high pumping rates, PVC tubing does not fully recover to its normal round uncompressed shape from a compressed condition rapidly enough to fill completely with fluid. Accordingly, the volumetric displacement of fluid within the PVC tubing that occurs with each pumping stroke is less than desired. To avoid this problem, tube shapers 50a and 50b force the pumping portion 34b of the flexible tubing to recover rapidly to its maximum volumetric capacity, i.e., to open sufficiently so that the desired amount of liquid 31 fills the pumping chamber defined by pumping portion 34b of the flexible tubing.

Each tube shaper 50a and 50b comprises an angled arm 234, terminating at one end in a longitudinally extending jaw 236. Arms 234 are attached to frame 100 at pivot mounts 230, about which arms 234 rotate as tubing shaper rollers 160 roll along inner surfaces 232 of arms 234. Thus, the reciprocating up-and-down motion of plunger 48 along its reciprocation axis inherently acts on tube shaper rollers 160 in "lock-step", causing jaws 236 to pinch pumping portion 34b of the flexible tubing at the proper time and thereby reforming flexible tubing 34 into the required pumping volume or capacity as plunger 48 lifts away from pressure plate 94.

In FIG. 5, tube shapers 50a and 50b are shown moving in opposite directions, away from pumping portion 34b of the flexible tubing as plunger 48 descends to compress flexible tubing 34 and displace fluid from the pumping portion. However, in FIG. 6, plunger 48 is shown moving upwardly away from pressure plate 94, acting on tube shaper rollers 160 to force opposing jaws 236 to swing inwardly toward each other in order to reshape pumping portion 34b of the flexible tubing, so that it achieves its desired volumetric capacity.

To further enhance the repeatability and consistency of the volumetric capacity defined in pumping portion 34b of the flexible tubing, plunger cam track 152 is sized and shaped so that plunger 48 never completely compresses pumping portion 34b of the flexible tubing, even at the lower most point of the plunger's reciprocal stroke. In addition, at the top of its reciprocal stroke, plunger 48 remains in contact with pumping portion 34b of the flexible tubing. The range of diametrical compression of flexible tubing 34 is from about 15% at the top of the pumping stroke to about 85% at the bottom of the pumping stroke of plunger 48. Since flexible tubing 34 need not recover to a fully uncompressed condition, i.e., to a perfect circular cross section, changes in the elasticity of flexible tubing 34 due to continued use and repeated compression have much less effect on the volumetric capacity of pumping portion 34b of the flexible tubing than would otherwise occur.

In order to calibrate tube shapers 50a and 50b so that their range of motion corresponds to that required to achieve proper reshaping of pumping portion 34b of the flexible tubing, a wedge-shaped slot 240 is provided in the upper outer portion of arms 234. To adjust the angle between the upper and lower portions of arms 234, a wedge-shaped insert 238 is driven into wedge-shaped slot 240, deflecting the upper portion of arm 234 through an angle, as indicated by reference numeral 242. Angle 242 is determined by use of an appropriate calibration jig (not shown), during manufacture of tube shapers 50a and 50b, or during assembly of these components in volumetric pump 30.

Details of inlet cracking valve 46 are shown in FIG. 8 and of outlet cracking valve 52, in FIG. 9. In these drawings, it is apparent that downwardly depending arms 136 straddle flexible tubing 34, and are spaced apart sufficiently so that blocks 204 and 210 of proximal pressure sensor 44 and distal pressure sensor 56 can fit therebetween. FIG. 8 more clearly illustrates side arm 116 and V-shaped side arm 118 at the top of inlet valve arm 108. In FIG. 9, the specific disposition of side arm 186 in respect to outlet valve cam follower 190, closure flexure 188, and cracking flexure 182 is also more clearly shown.

One of the advantages of using flat metal spring flexures, i.e., cracking flexure 112 and closure flexure 120, for biasing inlet valve arm 108 is that the force provided by each of these flexures is much more readily controlled than is typically the case with other types of spring assemblies. For example, by trimming the shape of these flexures or selecting flexures of a different thickness, the spring force they produce (i.e., their spring constant, K) can readily be modified and consistently controlled. The same advantages apply to the other flexures used in volumetric pump 30, such as inlet follower flexure 128 and balance block flexures 110. Accordingly, the cracking pressure and other characteristics of volumetric pump 30 can be precisely determined.

Figure 11:
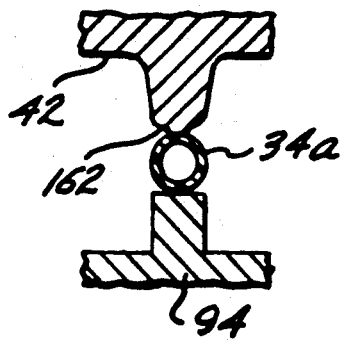
FIG. 11 is a cross-sectional view of the inlet cracking valve balance block where it acts on the flexible tubing.
Figure 12:
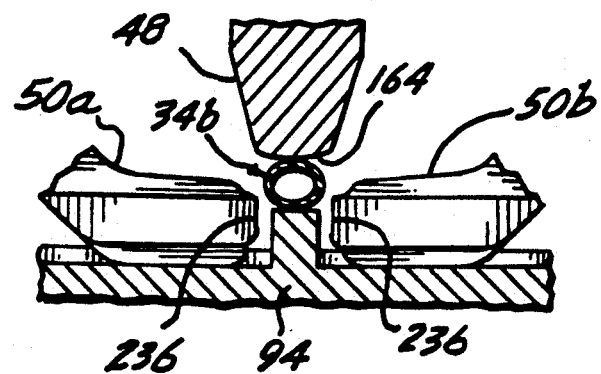
FIG. 12 is a cross-sectional view of part of the plunger and the flexible tubing.
Figure 13:
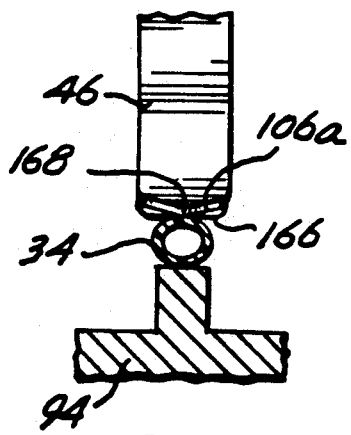
FIG. 13 is a cross-sectional view showing part of the inlet cracking valve in transverse profile.
Figure 14:
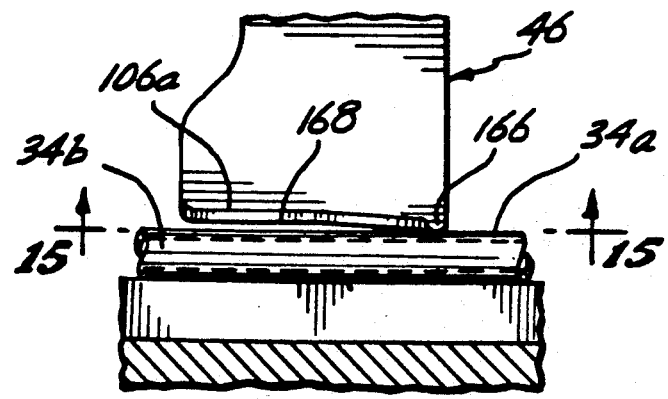
FIG. 14 is a cross-sectional view showing part of the inlet cracking valve in longitudinal profile.

A cross-sectional profile of balance block 42 is shown in FIG. 11. Similarly, in FIG. 12, a cross-sectional profile of plunger 48 is shown. It is instructive to compare the shape of a surface 162 on the bottom of balance block 42, which is in contact with proximal portion 34a of the flexible tubing, and a surface 164 on the bottom of plunger 48, which is in contact with pumping portion 34b of the flexible tubing with the profile of surface 106a on inlet cracking valve 46. A transverse view of valve face 106a is shown in FIG. 13, and its longitudinal profile is shown in FIG. 14. Balance block 42 generally rests upon proximal portion 34a of the flexible tubing, compressing the tubing slightly, but only to an extent determined by the stiffness of the tubing. To improve its responsiveness to the elasticity of flexible tubing 34, surface 162 of balance block 42 has a relatively narrow convex shape. In contrast, surface 164 of plunger 48 must substantially compress pumping portion 34b of the flexible tubing to displace fluid contained therein and its transverse cross section has a relatively blunt convex shape to better accomplish this function. To facilitate the responsiveness of inlet cracking valve 46 and outlet cracking valve 52 to fluid pressure in pumping portion 34b of the flexible tubing, their respective valve faces 106a and 106b have a substantially different transverse and longitudinal profile than either surface 162 or 164.

Figure 15:
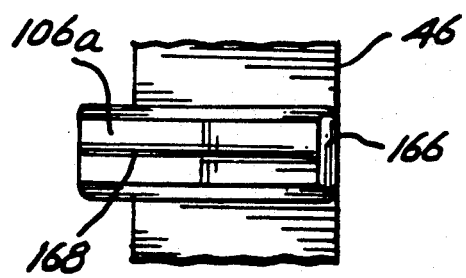
FIG. 15 is a plan view showing a surface of the inlet cracking valve that acts on the flexible tubing, taken generally along section line 15—15 in FIG. 14.

As shown in FIGS. 13, 14 and 15, valve face 106a comprises a longitudinal ridge 168 that intersects a transverse ridge 166 in a generally "T-shaped" formation. Particularly as shown in FIG. 14, transverse ridge 166 interdicts fluid flow through flexible tubing 34 when valve face 106a compresses flexible tubing 34. Compared to the rest of longitudinal ridge 168, the portion of that ridge adjacent to transverse ridge 166 extends outwardly from valve face 106a further or is more elevated. Fluid pressure building up within pumping portion 34b of the flexible tubing as a result of compression by plunger 48 acts through flexible tubing 34 along longitudinal ridge 168, developing a force that is the product of the fluid pressure and the area of longitudinal ridge 168. This force increases until it is sufficient to overcome the cracking force of inlet valve 46 that is compressing flexible tubing 34. A wedge of fluid from within pumping portion 34b of the flexible tubing builds up under longitudinal ridge 168, eventually forcing fluid flow past transverse ridge 166.

Both longitudinal ridge 168 and transverse ridge 166 have a radius of curvature that does not exceed a conforming curvature readily achievable by flexible tubing 34. Longitudinal ridge 168 is at least twice as long as the diameter of flexible tubing 34 to ensure that the pressure developed within the flexible tubing is applied over an area on valve face 106a sufficiently large to force inlet cracking valve 46 to pivot open at the desired predefined cracking pressure.

Valve face 106b on outlet cracking valve 52 has a similar "T-shaped" longitudinal conformation comprising longitudinal ridge 168 and transverse ridge 166. Furthermore, fluid within pumping portion 34b of the flexible tubing at the cracking pressure develops a force that acts over the area of longitudinal ridge 168 on valve face 106b to force open the outlet cracking valve, just as described above, in respect to inlet cracking valve 46. On both valve faces 106a and 106b, longitudinal ridge 168 is disposed farther from the pivot axes about which the cracking valves respectively pivot than transverse ridge 166, to increase the torque developed by the fluid within pumping portion 34b of the flexible tubing. At the cracking pressure, that torque thus exceeds the torque developed by the fluid control force, which is transmitted to flexible tubing 34 through transverse ridge 166. As noted previously, the pivot axes extend respectively through the center of pivot mounts 102 on inlet cracking valve 46, and through the center of pivot mounts 104 on outlet cracking valve 52.

Figure 10A:
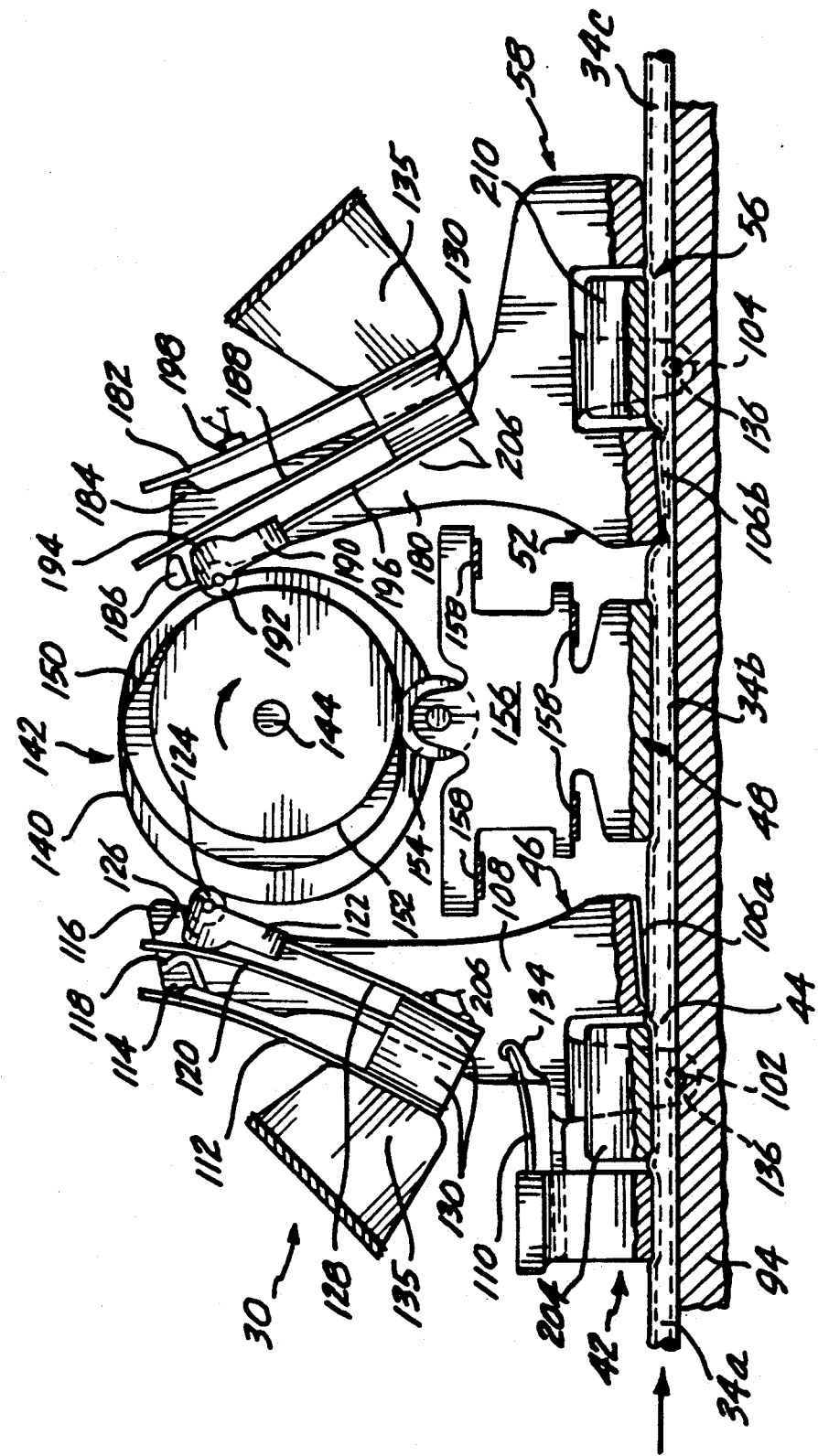
Figure 10B:
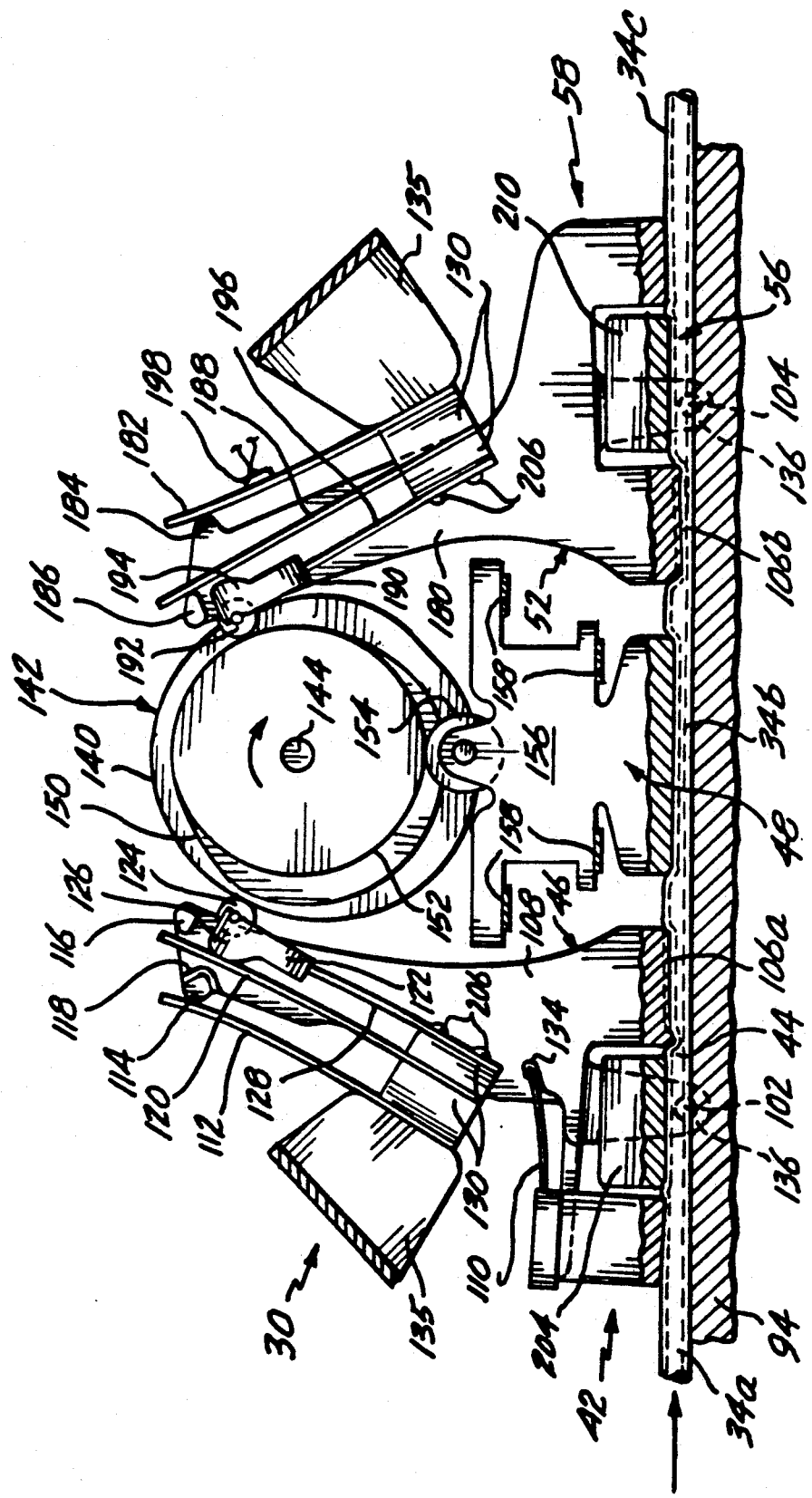

The operation of volumetric pump 30 can be readily understood by reference to FIGS. 10A, 10B, and 10C. In these figures, a less detailed longitudinal schematic view of volumetric pump 30 is shown from the opposite side, as compared to FIG. 4. Thus, in FIGS. 10A-10C, fluid enters volumetric pump 30 from the left side where proximal portion 34a of the flexible tubing is disposed, and exits toward the right, into distal portion 34c of the flexible tubing. The advantage of viewing the operation of volumetric pump 30 from this perspective is that the relative positions of cracking flexures 112 and 182, closure flexures 120 and 188, and cam followers 122 and 190 can readily be observed in respect to valve arms 108 and 180.

In FIG. 10A, volumetric pump 30 is shown with inlet cracking valve 46 in its open mode, wherein valve face 106a is lifted away from pressure plate 94 to permit fluid flow from container 32 into pumping portion 34b of the flexible tubing. This view corresponds to a fill segment of the pumping cycle. To achieve this configuration, cam assembly 142 rotates to a position where roller 124 contacts inlet cam track 140 at its maximum radial distance from cam shaft 144. Inlet cracking valve cam follower 122 is forced radially outward (to the left) sufficiently so that hood 126 contacts closure flexure 120, forcing it away from side arm 116 and into contact with V-shaped side arm 118, thereby pivoting inlet cracking valve 46 counterclockwise around pivot mounts 102. In this rotational position, roller 154 contacts plunger cam track 152 at its minimum radial profile, permitting plunger 48 to move reciprocally to its uppermost position, wherein the plunger maintains pumping portion 34b of the flexible tubing at approximately a 15% diametrical compression. Further, outlet cracking valve cam follower 190 is disposed at a minimum radial profile portion of outlet cam track 150, enabling closure flexure 188 to act on side arm 186. The combined force of closure flexure 188 and cracking flexure 182 pivot outlet valve arm 180 counterclockwise around pivot mounts 104, bringing transverse ridge 166 on outlet valve face 106b into compressive contact with flexible tubing 34 with enough force to completely close off fluid flow through the flexible tubing.

In FIG. 10B, cam assembly 142 has rotated into a pumpback-pressurization segment of the pumping cycle. During the pumpback-pressurization segment, outlet cracking valve 52 remains completely closed, as shown in FIG. 10A, while inlet cracking valve 46 is in its cracking mode. In the cracking mode, roller 124 contacts inlet cam track 140 at a point that defines an intermediate radius about camshaft 144. In this position, hood 126 of inlet cracking valve cam follower 122 lifts closure flexure 120 away from side arm 116 so that only cracking flexure 112 acts on inlet valve arm 108, producing most of the desired cracking force. As described above, the rest of the cracking force is developed by balance block 42, which provides a balance force that compensates for variations and changes in the stiffness or elasticity of flexible tubing 34 that might otherwise vary the desired cracking force.

During the pumpback-pressurization segment of the pumping cycle, plunger 48 descends from the top of the intake stroke, as shown in FIG. 10A, to the top of the pumping stroke, wherein pumping portion 34b of the flexible tubing is diametrically compressed by approximately 40%. As plunger 48 descends from the top of the intake stroke to the top of the pumping stroke, fluid pressure inside pumping portion 34b of the flexible tubing increases until it reaches a cracking pressure, at which point the force developed by the fluid pressure acting upon the surface of valve face 106a (more specifically, on the area of longitudinal ridge 168) is sufficient to overcome the cracking force, thereby opening inlet cracking valve 46, and allowing retrograde fluid flow through it from the pumping portion, back toward container 32. During the pumpback-pressurization segment of the pumping cycle, excess fluid within pumping portion 34b of the flexible tubing is thus forced back into proximal portion 34a of the flexible tubing. As the pumping segment of the pump cycle begins, only a predefined volume of fluid is contained within pumping portion 34b of the flexible tubing.

Finally, during a pumping segment of the pumping cycle that is represented in FIG. 10C, cam assembly 142 rotates to a point wherein roller 124 contacts inlet cam track 140 at a minimum radius about camshaft 144, such that inlet cracking valve cam follower 122 is no longer in contact with closure flexure 120. Under this condition, both cracking flexure 112 and closure flexure 120 act upon inlet valve arm 108, producing a total force that causes valve face 106a (i.e., transverse ridge 166) to compress flexible tubing 34 against pressure plate 94, thereby completely blocking fluid flow past inlet cracking valve 46 in either direction.

Meanwhile, outlet cracking valve 52 switches to its cracking mode, as hood 194 on the outlet valve follower 190 lifts closure flexure 188 away from side arm 186 so that the closure flexure no longer applies a force against outlet valve arm 180. In this configuration, cracking flexure 182 provides most of the predefined cracking force acting on transverse ridge 166 to compress flexible tubing 34 against pressure plate 94 at outlet valve face 106b. Balance block 58 provides the remainder of the predefined cracking force, compensating for variations in the stiffness or elasticity of flexible tubing 34, and thereby preventing such variations from affecting the desired predefined cracking force. Plunger 48 continues to descend, further compressing pumping portion 34b of the flexible tubing. Fluid pressure within the pumping portion is already at the desired cracking pressure from the pumpback-pressurization segment of the pumping cycle, and this cracking pressure acts on the area of longitudinal ridge 168 at valve face 106b, immediately creating a force that exceeds the cracking force of outlet cracking valve 52. The cracking pressure of the fluid (liquid 31) causes outlet cracking valve 52 to pivot clockwise about pivot mounts 104 sufficiently to enable fluid flow into distal portion 34c of the flexible tubing. Plunger 48 continues to descend until it reaches approximately 85% diametrical compression of pumping portion 34b of the flexible tubing. At this point, a predefined volume of fluid, e.g., 100 microliters, at a predefined cracking pressure has been displaced from volumetric pump 30 into distal portion 34c of the flexible tubing.

From the preceding explanation, it should be apparent that each pumping cycle of volumetric pump 30 includes three distinct segments: (1) a fill segment during which a pumping chamber defined between inlet cracking valve 46 and outlet cracking valve 52, i.e., the volume within pumping portion 34b of the flexible tubing, fills with fluid; (2) a pumpback-pressurization segment, wherein excess fluid within the pumping portion of the flexible tubing is forced back into proximal portion 34a of the flexible tubing, toward container 32 as the fluid is pressurized to the cracking pressure; and (3) a pumping segment, wherein fluid within the pumping portion of the flexible tubing at the cracking pressure is forced from volumetric pump 30 into distal portion 34c of the flexible tubing. Although not shown, a pump controller controls volumetric pump 30 in accordance with a plurality of program steps to effect the pumping cycle.

While the present invention has been disclosed in respect to a preferred embodiment, those of ordinary skill in the art will appreciate that further changes may be made thereto consistent with the scope of the claims that follow below. Accordingly, applicants do not intend that the disclosure of the preferred embodiment in any way limit the invention, but that the scope of the invention be determined entirely by reference to the claims that follow.

The invention in which an exclusive property or privilege is claimed is defined as follows:

1. A valve for controlling fluid flow through a passage defined by an elastomeric member, comprising:

a. a frame, said frame including backing means for supporting the elastomeric member;
b. a valve member that is pivotally mounted to the frame to rotate about a pivot axis and is generally positioned on an opposite side of the passage from the backing means, said valve member including:
   (1) flow control means for:
      (a) closing the passage by compressing the elastomeric member against the backing means with a cracking force that is independent of any external load applied to the valve member,
      (b) blocking fluid flow through the passage until the pressure of a fluid within the passage exceeds a predetermined cracking pressure sufficient to force open the passage, and
      (c) regulating the pressure of fluid thus flowing through the passage to the cracking pressure;
   (2) force balance means, disposed generally on an opposite side of the pivot axis from the flow control means and in contact with the elastomeric member but incapable of blocking flow through the passage, for:
      (a) developing a force as a result of contact with the elastomeric member that adds to the cracking force by an amount that depends on an elasticity of the elastomeric member, and
      (b) compensating for any variations in the elasticity that would otherwise vary the cracking pressure; and
c. a spring mounted between the frame and the valve member, said spring contributing to the cracking force exerted against the elastomeric member by the flow control means.

2. The valve of claim 1, wherein the elastomeric member comprises flexible tubing.

3. The valve of claim 1, further comprising closure means for pivoting the valve member so that the flow control means compresses the elastomeric member, closing the passage with a relatively greater force than the cracking force, preventing fluid flow through the passage even though the pressure of fluid within the passage substantially exceeds the cracking pressure.

4. The valve of claim 3, wherein the closure means comprises a second spring mounted between the housing and the valve member, which is selectively controlled to increase the force applied by the valve member to compress the elastomeric member sufficiently to block fluid through the passage.

5. The valve of claim 1, wherein the valve member further includes a spring link connecting a first portion of the valve member on which the flow control means is disposed to a second portion of the valve member on which the force balance means is disposed.

6. The valve of claim 5, wherein the spring link comprises a thin metal flexure that bends with sufficient elasticity to enable the first portion of the valve member to assume a position in which the passage between the first portion of the valve member and the backing means is open, independent of fluid pressure, said first portion of the valve member pivoting further away from the elastomeric member than the second portion, leaving the passage substantially open and the elastomeric member substantially uncompressed both between the flow control means and the backing means and between the force balance means and the backing means.

7. The valve of claim 6, further comprising means for pivoting the flow control means away from the elastomeric member, in opposition to the cracking force, to open the passage.

8. A cracking valve for use in a pump that positively displaces fluid by compressing a pumping portion of flexible tubing against a backing member until the pressure of the fluid within the compressed pumping portion exceeds a predetermined cracking pressure, said cracking pressure being defined as a fluid pressure of sufficient magnitude to force the cracking valve to open, permitting the fluid to flow from the pump, comprising:
   valve member means, mounted to the pump adjacent the flexible tubing so as to pivot about a pivot axis, for regulating the pressure of fluid flowing past the valve member means to the cracking pressure, independent of any externally applied load, said valve member means including:
      flow control means disposed proximal to the pumping portion of the flexible tubing that is compressed, for compressing the flexible tubing against the backing member with a cracking force, and
      force balance means disposed distal to the pumping portion of the flexible tubing that is compressed and continuously in contact with the flexible tubing but substantially incapable of limiting fluid flow through it, for compensating the cracking force for variations in an elasticity of the flexible tubing, the flow control means and the force balance means tending to pivot the valve member means in opposite directions in reaction to the elasticity of the flexible tubing; and
   spring means for biasing the valve member means to pivot about the pivot axis so that the flow control means compress the flexible tubing against the backing member with the cracking force, the force balance means and the spring means thus determining the cracking force so that its magnitude is independent of any load applied to the valve member means.

9. The cracking valve of claim 8, wherein the valve member means is generally "Y" shaped, having first, second, and third legs joined together, and wherein the flow control means and force balance means are disposed on the first and second legs, respectively.

10. The cracking valve of claim 9, wherein a vertex of the valve member at which the first, second, and third legs are joined is connected to pivot arms that extend laterally from opposite surfaces of the "Y-shaped" section, said pivot axis being disposed within the pivot arms.

11. The cracking valve of claim 8, wherein the third leg is actuated by a profiled rotating cam surface, the rotating cam surface selectively changing the compression force exerted by the flow control means against the flexible tubing during a pumping cycle so that the cracking force is not applied.

12. The cracking valve of claim 8, wherein the spring means comprise a flexure that is mounted so as to apply a spring bias against the valve member means, causing it to compress the flexible tubing with the flow control means.

13. The cracking valve of claim 8, wherein the spring means comprise a plurality of springs that each contribute to a force biasing the valve member means to pivot about the pivot axis so as to move the flow control means toward the flexible tubing, one of the springs providing a closure force that substantially exceeds that required to determine the cracking pressure, said one spring causing the flow control means to completely block fluid flow through the flexible tubing, independently of the cracking pressure.

14. The cracking valve of claim 8, further comprising means for moving the flow control means away from the backing member so as to open a passage through the flexible tubing.

15. The cracking valve of claim 14, further comprising a flexure connecting the force balance means to the flow control means, said flexure enabling the valve member means to pivot the flow control means away from the backing member to open the flexible tubing without causing the force balance means to compress the flexible tubing sufficiently to significantly block fluid flow therethrough.

16. The cracking valve of claim 15, wherein the valve member means is disposed on an inlet side of said pumping portion of the flexible tubing in respect to a source of the fluid and serves as an inlet valve for the pump.

17. The cracking valve of claim 8, wherein the valve member means is disposed on an outlet side of said pumping portion of the flexible tubing with respect to a source of the fluid and serves as an outlet valve for the pump.

18. A method for compensating a cracking valve for variations in the elasticity of a flexible member that defines a passage through which fluid is pumped due to positive displacement of a pumping portion of the flexible member, said method thereby maintaining a generally constant cracking pressure in the fluid pumped, comprising the steps of:
  in response to the elasticity of the flexible member, producing a balancing force; and
  adding the balancing force to a flow control force exerted by the cracking valve against the flexible member, producing a cracking force tending to close off the passage, where said cracking force is determinative of a cracking pressure required in the fluid to force open the cracking valve and enable a fluid flow through the passage, thereby preventing any change in the cracking pressure and volume of the fluid displaced from the pumping portion of the flexible member that would otherwise occur due to a variation in the elasticity of the flexible member affecting its resistance to the cracking force.

19. The method of claim 18, further comprising the step of applying a closure force to the cracking valve sufficiently great to block fluid flow through the passage, independently of the cracking pressure.

20. The method of claim 18, further comprising the step of providing a flexure in the cracking valve, said step of producing the balancing force comprising the step of contacting the flexible member with a balance block that is connected to the cracking valve by the flexure, said flexure elastically bending and thus preventing closure of the passage through the flexible member by the balance block as the cracking valve opens to enable fluid to flow into the pumping portion of the flexible member.

21. A cracking valve for controlling the flow of a pressurized fluid through a flexible tubing, comprising:
  a pivotally mounted valve member including an elongate surface for applying a compressive force to the flexible tubing, said surface comprising a generally "T" shaped formation that contacts the flexible tubing, said formation being defined by a transverse ridge and a longitudinal ridge, the longitudinal ridge being generally aligned with a longitudinal axis of the flexible tubing and the transverse ridge being generally transverse to said longitudinal axis; and
  a spring for biasing the valve member to pivot the surface into contact with the flexible tubing with a flow control force sufficient for the transverse ridge to block fluid flow through the flexible tubing until the pressure of the fluid exceeds a predetermined cracking pressure, said pressure of the fluid within the flexible tubing acting through the flexible tubing over an area of said surface encompassing the longitudinal ridge to achieve a force that exceeds the flow control force, thereby opening a passage in the flexible tubing through which fluid flows past the transverse ridge.

22. The cracking valve of claim 21, wherein the transverse and longitudinal ridges are defined at least in part by curves having radii that do not exceed a conforming curve readily achievable by the flexible tubing.

23. The cracking valve of claim 21, wherein the transverse ridge is disposed on the surface so as to contact the flexible tubing at a point more distal from the pressurized fluid than where the longitudinal ridge contacts the flexible tubing.

24. The cracking valve of claim 21, wherein the longitudinal ridge is at least twice as long as the diameter of the flexible tubing.

25. The cracking valve of claim 21, wherein the longitudinal ridge extends outwardly of said surface of the valve member with an elevation that is greater proximal the transverse ridge than distal thereto.

26. The cracking valve of claim 21, wherein the valve member further comprises means for compensating for variations in the elasticity of the flexible tubing to minimize changes in the cracking pressure.

27. The cracking valve of claim 26, wherein the means for compensating comprise a second surface in contact with the flexible tubing, said second surface being disposed on an opposite side of a pivot axis about which the valve member pivots.

28. The cracking valve of claim 26, wherein the means for compensating comprise a force balance surface that contacts the flexible tubing along a section that is spaced apart from that where the surface of the valve member contacts it and disposed on an opposite side therefrom in respect to a pivot axis of the valve member, said force balance surface transmitting a compensating balance force having a magnitude that is a function of the elasticity of the flexible tubing, through the valve member, said balance force being added to the flow control force provided by the spring to provide a cracking force.

29. The cracking valve of claim 21, where the longitudinal ridge is disposed farther from a pivot axis about which the valve member pivots than the transverse ridge to increase the torque developed by the cracking pressure so that it exceeds the torque developed by the flow control force that acts to compress the flexible tubing with the transverse ridge.

30. The cracking valve of claim 29, wherein the cracking pressure acts on the longitudinal ridge through the flexible tubing to force the transverse ridge away from a backing member against which the transverse ridge is compressing the flexible tubing, thereby enabling fluid to flow through the flexible tubing past the transverse ridge.

* * * * *